United States Patent [19]

Lin et al.

[11] Patent Number: 5,716,630
[45] Date of Patent: Feb. 10, 1998

[54] PESTICIDAL TABLET FORMULATIONS

[75] Inventors: Kang-Chi Lin, Lafayette; Derek A. Stonich, San Jose; Ralph L. Barnett, Antioch, all of Calif.

[73] Assignee: Zeneca Limited, London, England

[21] Appl. No.: 668,486

[22] Filed: Jun. 21, 1996

[51] Int. Cl.[6] .................................................. A01N 25/22
[52] U.S. Cl. ............................................. 424/408; 424/405
[58] Field of Search ........................... 43/124; 424/464, 424/408, 466

[56] References Cited

U.S. PATENT DOCUMENTS

| | | | |
|---|---|---|---|
| 4,013,820 | 3/1977 | Farhadieh et al. | 424/35 |
| 5,180,587 | 1/1993 | Moore | 424/465 |
| 5,306,499 | 4/1994 | Ohtsubo et al. | 424/405 |
| 5,338,551 | 8/1994 | Lajoie | 424/405 |
| 5,516,520 | 5/1996 | Yang et al. | 424/408 |
| 5,516,529 | 5/1996 | Zellweger | 424/466 |

*Primary Examiner*—Neil B. Levy
*Attorney, Agent, or Firm*—Joel G. Ackerman

[57] ABSTRACT

Noneffervescent pesticidal tablets containing from about 0.1 to about 30 weight percent of a pesticide, from about 0.5 to about 50 weight percent microcrystalline cellulose, from about 5 to about 50 weight percent urea, and from about 0.1 to about 10 weight percent of one or more organic carboxylic acids. The tablets may be packaged in water-soluble film.

10 Claims, No Drawings

PESTICIDAL TABLET FORMULATIONS

BACKGROUND AND PRIOR ART

This invention relates to novel pesticidal formulations in the form of tablets, particularly tablets which are well dispersible in water but which are noneffervescing. The term "well dispersible in water" is meant to indicate that the tablets begin disintegration immediately in water at ambient conditions (5°–25° C.) and completely disintegrate in less than 5 minutes, preferably less than 3 minutes.

Literature contains many examples of tableted formulations of pesticides which are designed to be dispersible or dissolvable in water. Many, if not most, of them are effervescent, that is they contain a combination of an organic acid and a base which combined form carbon dioxide when the tablet is exposed to contact with water. This effervescent quality is believed to contribute to rapid dispersibility or dissolvability of such tablets in water. However, it can have the disadvantage of producing undesired early disintegration of stored tablets should they come into contact with moisture. For example, even tablets which are packaged in water-soluble film can begin to disintegrate at an undesirably early stage because of seepage of moisture into the package.

SUMMARY OF THE INVENTION

This invention comprises pesticidal formulations in the tablet form comprising: (a) from about 0.1 to about 30 weight percent of a pesticide; (b) from about 0.5 to about 50 weight percent microcrystalline cellulose; (c) from about 0.1 to about 10 weight percent of one or more organic carboxylic acids; (d) from about 5 to about 50 weight percent urea.

DETAILED DESCRIPTION OF THE INVENTION

The invention provides pesticidal tablet formulations which contain from about 0.5 to about 30, preferably from about 10 to about 25 weight percent of a pesticide, from about 0.5 to about 50 weight percent microcrystalline cellulose, from about 0.1 to about 10 weight percent of one or more organic carboxylic acids, and from about 5 to about 50 weight percent of urea. The remainder of the tablet comprises typical ingredients utilized in such formulations such as surfactants, lubricants, fillers, etc.

The pesticide may be, for example, an insecticide, fungicide, herbicide, insect growth regulator, or herbicidal plant growth regulator. Preferably the pesticide contained in these formulations is a water-insoluble pesticide, but water-soluble pesticides are included within the concept of this invention. The tablets of this invention may contain a single pesticide, or a combination of pesticides and may contain other ingredients such as fertilizers, if the tablets are intended for agricultural or home and garden use.

In a preferred embodiment, the tablets contain an insecticide and are designed for use in controlling insects in and around buildings and other structures. Such tablets are conveniently packaged in small packages or, alternatively, in water-soluble pouches from which they may be dispensed into portable spray tanks for use by pest control operators in spraying the insecticide in areas to be treated. The term "tablet" is meant to include what is conventionally regarded as a tablet as well as other solid compaction forms such as briquettes and pellets.

In addition to being well dispersible in water, the tablets of this invention also possess good storage stability.

Examples of suitable pesticides for use in the formulations of this invention include both organophosphorus and pyrethroid insecticides such as fonofos, lambda-cyhalothrin, permethrin, cypermethrin, deltamethrin, or tefluthrin; herbicides such as atrazine or sulfonyl ureas and fungicides such as azoxystrobin.

The tablets contain from about 0.5 to about 50 weight percent, preferably from about 1 to about 20 weight percent of microcrystalline cellulose. The use of such material in pesticide tablet formulations is described in a 1992 publication of Ibrahim et at. entitled "Compressed Tablets as a Potential Pesticide Delivery System," Pesticide Formulations And Application Systems: Eleventh Volume, ASTM STP1112. The microcrystalline cellulose used is typically a free flowing white powder available in several particle sizes. Microcrystalline cellulose has been used extensively in the formulation of tablets used in the pharmaceutical industry. It acts as a binding agent imparting increased tablet strength without excessive compressive force. One suitable material is microcrystalline cellulose sold by FMC under the trademark LATTICE.

The formulations of this invention contain from about 5 to about 50, preferably from about 10 to about 40, weight percent of urea, which functions as a filler.

Also contained in these tablets is from about 0.1 to about 10, preferably from about 0.5 to about 5, weight percent of one or more organic carboxylic acids, preferably citric acid or a combination of citric and another organic acid. Citric acid is a well known ingredient in many effervescent pesticidal tablet formulations in which, in combination with a base such as sodium carbonate or bicarbonate, it produces carbon dioxide to cause effervescence. Other suitable organic acids include stearic, maleic, succinic, and tartaric acids.

The tablets are prepared by the usual tableting methods, namely, conversion of a mixture of ingredients. They may be produced by either direct compression or by granulation followed by tableting. A general process would include the impregnation of a carrier with the active ingredient or ingredients as necessary and blending with inert ingredients. The mixture could be converted directly into tablets or further processed prior to producing tablets.

The following example is illustrative of the invention:

EXAMPLE 1

The pesticide utilized was technical grade (85.4% purity) lambda-cyhalothrin. Other ingredients used were anionic surfactant and nonionic surfactants, Agrimer 30 (polyvinylpyrrolidone, ISP), Ac-Di-Sol (cross linked sodium carboxy methyl cellulose, FMC), Wessalon S (silica carrier, Degussa), wetting and dispersing agents, Lattice NT50 (microcrystalline cellulose, FMC), Cab-O-Sil M-5 (fumed silica, Cabot Corp.), stearic acid, citric acid, talc and urea.

The amounts of ingredients are shown in the following table:

| Ingredient | Wt., g | Wt. % |
| --- | --- | --- |
| Lambda-cyhalothrin, technical grade | 11.70 | 11.70 |
| Anionic and nonionic surfactants | 2.71 | 2.71 |
| Wessalon S | 11.80 | 11.80 |
| Agrimer 30 | 1.44 | 1.44 |
| Ac-Di-Sol | 1.93 | 1.93 |
| Urea | 41.16 | 41.16 |

-continued

| Ingredient | Wt., g | Wt. % |
|---|---|---|
| Citric Acid | 1.00 | 1.00 |
| Wetting and dispersing agents | 2.56 | 2.56 |
| Lattice NT50 | 22.47 | 22.47 |
| Cab-O-Sil M-5 | 0.43 | 0.43 |
| Talc | 2.00 | 2.00 |
| Stearic Acid | 0.80 | 0.80 |

The tablets were prepared by the following process: The lambda-cyhalothrin technical is blended with the liquid anionic and nonionic surfactants. The mixture is applied to the carrier Wessalon S and blended. Dry surfactants, Agrimer 30, Ac-Di-Sol, urea and citric acid are added and blended until homogenous. The material is then milled using a hammer mill fitted with a 1 mm screen. The milled premix and the remaining ingredients with the exception of stearic acid, are mixed for at least 10 minutes. The stearic acid is added prior to tableting and the mixture is mixed no more than five minutes. Typically the density of the premix will be increased by slugging using a tablet press fitted with flat faced tooling. The granulate is produced using a screen of 10–18 mesh. Tablets having the desired physical properties are then produced using this granulate.

Dispersibility of the tablets was tested by the following procedure: Approximately 800 ml of tap water at room temperature is added to a container having a top which can be sealed. The tablet is added and the top sealed. The disintegration of the tablet is observed. For Example 1, the tablet fell to the bottom of the container and began to disintegrate. The tablet was observed to completely disintegrate in less than 3 minutes.

What is claimed is:

1. A noneffervescent pesticidal tablet comprising (a) from about 0.1 to about 30 weight percent of a pesticide; (b) from about 0.5 to about 50 weight percent microcrystalline cellulose; (c) from about 5 to about 50 weight percent urea; and (d) from about 0.1 to about 10 weight percent of one or more organic carboxylic acids.

2. A tablet according to claim 1 comprising (a) from about 10 to about 25 weight percent of a pesticide; (b) from about 1 to about 20 weight percent of microcrystalline cellulose; (c) from about 10 to about 40 weight percent urea; and (d) from about 0.5 to about 5 weight percent one or organic carboxylic acids.

3. A composition according to claim 1 in which the pesticide is an insecticide.

4. A composition according to claim 3 in which the insecticide is a pyrethroid.

5. A composition according to claim 4 in which the pyrethroid is lambda cyhalothrin.

6. A composition according to claim 1 containing two or more pesticides.

7. A composition according to claim 1 in which the organic carboxylic acids comprise citric acid.

8. A composition according to claim 1 enclosed within a water soluble film.

9. A method of controlling pests or undesired vegetation comprising applying to said pest, said vegetation, or the locus thereof, a composition according to claim 1.

10. A method of controlling pests or undesired vegetation comprising applying to said pest, said vegetation, or the locus thereof, a composition according to claim 8.

* * * * *